(12) United States Patent
Kuramitsu et al.

(10) Patent No.: US 9,199,862 B2
(45) Date of Patent: Dec. 1, 2015

(54) METHOD FOR ADSORBING FLUOROCARBOXYLIC ACID HAVING ETHER BOND AND METHOD FOR COLLECTING SAME

(75) Inventors: Masaki Kuramitsu, Settsu (JP); Takuya Ichida, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 99 days.

(21) Appl. No.: 13/260,558

(22) PCT Filed: Mar. 24, 2010

(86) PCT No.: PCT/JP2010/055073
§ 371 (c)(1),
(2), (4) Date: Sep. 26, 2011

(87) PCT Pub. No.: WO2010/113720
PCT Pub. Date: Oct. 7, 2010

(65) Prior Publication Data
US 2012/0029232 A1  Feb. 2, 2012

(30) Foreign Application Priority Data
Mar. 31, 2009 (JP) .................. 2009-084535

(51) Int. Cl.
| | |
|---|---|
| *B01J 20/20* | (2006.01) |
| *B01J 20/28* | (2006.01) |
| *B01J 20/34* | (2006.01) |
| *C02F 1/28* | (2006.01) |
| *C07C 51/47* | (2006.01) |
| *C02F 1/66* | (2006.01) |
| *C02F 101/36* | (2006.01) |

(52) U.S. Cl.
CPC .............. *C02F 1/283* (2013.01); *B01J 20/20* (2013.01); *B01J 20/28004* (2013.01); *B01J 20/28066* (2013.01); *B01J 20/3416* (2013.01); *B01J 20/3475* (2013.01); *C07C 51/47* (2013.01); *C02F 1/66* (2013.01); *C02F 2101/36* (2013.01); *C02F 2209/02* (2013.01); *C02F 2303/16* (2013.01)

(58) Field of Classification Search
CPC ............... B01J 20/20; B01J 20/28004; B01J 20/28066; B01J 20/3416; B01J 20/3475; C02F 1/283; C07C 51/47
USPC ........................................................ 562/580
See application file for complete search history.

(56) References Cited

U.S. PATENT DOCUMENTS

| | | | | |
|---|---|---|---|---|
| 4,508,851 | A | * | 4/1985 | Izumi et al. ................ 502/426 |
| 5,883,040 | A | * | 3/1999 | Armstrong et al. ........... 502/437 |
| 2004/0010156 | A1 | | 1/2004 | Kondo et al. |
| 2007/0068869 | A1 | | 3/2007 | Yamasaki et al. |
| 2010/0197964 | A1 | * | 8/2010 | Kuramitsu ................... 562/605 |

FOREIGN PATENT DOCUMENTS

| | | | | |
|---|---|---|---|---|
| CN | 101332992 | A | | 12/2008 |
| EP | 1323677 | A1 | | 7/2003 |
| GB | 949285 | | * | 2/1964 |
| JP | 9-315809 | A | | 12/1997 |
| JP | 2000-143552 | | * | 5/2000 |
| JP | 2000256006 | A | | 9/2000 |
| JP | 2002059160 | A | | 2/2002 |
| JP | 2003012316 | A | | 1/2003 |
| JP | 2003094052 | A | | 4/2003 |
| JP | 2005329328 | A | | 12/2005 |
| JP | 2006-181416 | | * | 7/2006 ............... B01J 20/30 |
| JP | 2006181416 | A | | 7/2006 |
| JP | 2007090206 | A | | 4/2007 |
| JP | WO2009/031562 | | * | 3/2009 ............... B01J 20/34 |
| WO | 2009031562 | A1 | | 3/2009 |

OTHER PUBLICATIONS

Baker et al., 2003. Carbon, Activated. Kirk-Othmer Encyclopedia of Chemical Technology, pp. 741-761.*
Wankat et al., Process for Recovery of Solvent Vapors with Activated Carbon, Ind. Eng. CHem. Process Des. Dev. 19, 446-451 (1980).*
Wang et al., "Effect of pH adjustment Upon Activated Carbon Adsorption of Dissolved Organics From Industrial Effluents," Enginerring Extension Series (Purdue University), 141, Pt. 1, 569-78, 1972.*
Caporiccio et al., "Some Physiochemical Properties of Perfluoropolyether Surfactants," Journal of Colloid and Interface Science, vol. 98, No. 1, Mar. 1984, pp. 202-209.*
Translation of JP2000-143552.*
Buschow, K.H. Jürgen Cahn, Robert W. Flemings, Merton C. Ilschner, Bernhard Kramer, Edward J. Mahajan, Subhash (2001). Encyclopedia of Materials—Science and Technology, vols. 1-11. Elsevier).*
Ochoa-Herrera, et al., Removal of perfluorinated surfactants by sorption onto granular activated carbon, zeolite, and sludge, Chemosphere, 72 (2008) 1588-1593.*
Extended European Search Report issued in corresponding European Application No. 10758494.8, dated Sep. 12, 2013.

* cited by examiner

*Primary Examiner* — Paul A Zucker
*Assistant Examiner* — Mark Luderer
(74) *Attorney, Agent, or Firm* — Sughrue Mion, PLLC

(57) ABSTRACT

Disclosed are an adsorption process whereby a fluorocarboxylic acid having an ether bond can be adsorbed to a high extent by using active carbon without changing the form thereof, and a desorption process whereby the adsorbed material can be desorbed from the active carbon to thereby enable the reuse of the active carbon and the adsorbed material. In the aforesaid processes, a solution containing a fluorocarboxylic acid having an ether bond is contacted with active carbon and thus the active carbon is allowed to adsorb the fluorocarboxylic acid, to thereby give a solution having a small fluorocarboxylic acid content. Then, the active carbon having adsorbed the fluorocarboxylic acid is heated to thereby desorbs the fluorocarboxylic acid from the active carbon.

16 Claims, 1 Drawing Sheet

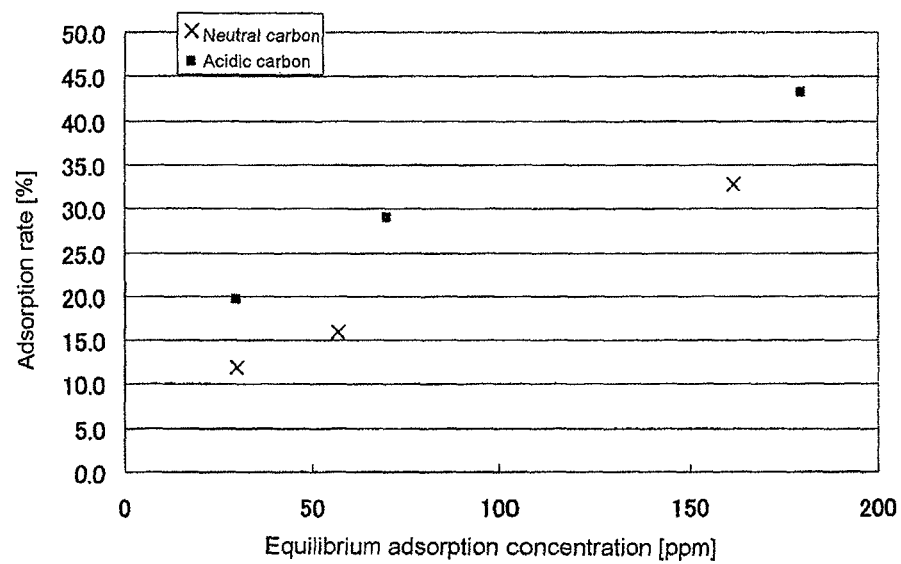

METHOD FOR ADSORBING FLUOROCARBOXYLIC ACID HAVING ETHER BOND AND METHOD FOR COLLECTING SAME

CROSS REFERENCE TO RELATED APPLICATIONS

This application is a National Stage of International Application No. PCT/JP2010/055073 filed Mar. 24, 2010, claiming priority based on Japanese Patent Application No. 2009-084535 filed Mar. 31, 2009, the contents of all of which are incorporated herein by reference in their entirety.

FIELD OF THE INVENTION

The present invention relates to a method of adsorbing a fluorocarboxylic acid having an ether bond, in which the fluorocarboxylic acid having an ether bond contained in a liquid phase is capable of being highly collected, and a method of recovering the fluorocarboxylic acid, in which the fluorocarboxylic acid is capable of being highly recovered from an active carbon.

According to the present invention, it is capable of efficiently and selectively recovering the fluorocarboxylic acid having an ether bond from a liquid phase, such as waste water from a plant, waste water from households and rivers. In addition, it is capable of recycling active carbon and recovering the adsorbed substances by desorbing the adsorbed substances from the active carbon which has adsorbed.

BACKGROUND OF THE INVENTION

A fluorocarboxylic acid having an ether bond, for example, 2,3,3,3-tetrafluoro-2-[1,1,2,3,3,3-hexafluoro-2-(trifluoromethoxy)propoxy]-propanoic acid has a solubility in water of about 10% at normal temperature, which is about 50 times of the solubility of perfluorooctanoic acid (PFOA) in water. Therefore, the adsorption rate of general active carbon, for example, general-purpose active carbon for waste water which was conventionally used is 5% or less at normal temperature and pH 7.

It was difficult to highly adsorb the fluorocarboxylic acid having an ether bond, which has high solubility in water, with using the conventional active carbon having a specific surface area of 1,000 m$^2$/g or less. Such adsorption method was associated with problems of cost.
Patent Document 1: JP-A-09-315809

DISCLOSURE OF THE INVENTION

Problems to be Solved by the Invention

An object of the present invention is to provide a method of highly adsorbing a fluorocarboxylic acid having an ether bond and a method of recovering the fluorocarboxylic acid.

Means for Solving the Problem

The present invention is based on the fact that the fluorocarboxylic acid having an ether bond is highly adsorbed by an active carbon which has been subjected to a particular treatment.

The present invention provides a method of adsorbing a fluorocarboxylic acid having an ether bond, wherein the fluorocarboxylic acid is adsorbed by an active carbon by contacting a liquid containing the fluorocarboxylic acid with the active carbon. The method of adsorbing the fluorocarboxylic acid may be used for a method of treating a liquid which contains the fluorocarboxylic acid.

The present invention further provides a method of desorbing the fluorocarboxylic acid having an ether bond without decomposition of the fluorocarboxylic acid, wherein the fluorocarboxylic acid is desorbed from the active carbon by heating the active carbon, which has adsorbed the fluorocarboxylic acid, to a temperature of 99° C. to 145° C.

It is capable to recover the fluorocarboxylic acid by collecting the desorbed fluorocarboxylic acid.

Effect of the Invention

According to the present invention, it is capable to highly adsorb the fluorocarboxylic acid having an ether bond. In the desorbing process, it is capable to recycle the active carbon by heating the active carbon to a temperature of 99° C., which is suitable for desorption by azeotropy with water and avoids heat decomposition of the fluorocarboxylic acid having an ether bond. It is capable to recycle the fluorocarboxylic acid by collecting and concentrating the desorbed fluorocarboxylic acid.

BRIEF DESCRIPTION OF THE DRAWING

FIG. 1 is a graph showing the relationship between an adsorption rate and an equilibrium concentration in the cases using a high activation active carbon adjusted to hydrochloric acid acidity and a high activation active carbon adjusted to neutral prepared in Example 5.

MODE OF CARRYING OUT THE INVENTION

Preferably, in the present invention, the active carbon is highly activated in order to improve the physical adsorptivity of the active carbon and the specific surface area of the active carbon is increased to 1500 m$^2$/g or more. Preferably, the chemical adsorptivity of the active carbon is also improved by impregnating the surface of the active carbon with an ion. The adsorption rate of the active carbon can be improved to 100 or more, for example 20% or more.

The adsorption rate (%) is given by:

[[(Concentration of fluorocarboxylic acid in initial raw water [ppm])−(Concentration of fluorocarboxylic acid in treated water after adsorption [ppm])]×(Amount of raw water [g])]/[(Amount of used active carbon [g])×1,000,000]×100 [%].

The active carbon to be used for the present invention can be produced from carbonaceous materials. As the carbonaceous material, a material which produces an active carbon by carbonization or activation can be used. Such material includes, for example, materials of plant origin such as woods, sawn wood, charcoal, coconut shell, fruit shell such as walnut shell and seeds of fruits; materials of mineral origin, for example, coal such as peat, lignite, brown coal, bituminous coal and anthracite coal, pitch such as petroleum pitch and coal pitch, cokes, tar such as coal tar and petroleum tar, petroleum distillates residues; natural materials, for example, cellulosic fiber such as cotton and rayon, and synthetic materials such as phenolic resin, polyvinyl alcohol and polyacrylonitrile. The form of the active carbon and the carbonaceous material includes powder form, granular form, fibrous form and any form which is prepared by molding the material.

An active carbon can be produced from the carbonaceous material by subjecting the carbonaceous material to a treatment such as carbonization or activation. The carbonization may be performed by, for example, heat retorting the carbonaceous material at a temperature between about 300 and 700° C. The activation may be performed by, for example, medicament activation using, for example, zinc chloride, phosphoric acid, sulfuric acid, calcium chloride, sodium hydroxide or potassium hydroxide, gas activation using, for example, steam, carbon dioxide, oxygen gas, combustion exhaust gas or a mixture gas thereof. The size of the active carbon is generally in a range between 0.5 and 5.0 mm. Specific surface area of the active carbon can be increased by an activation. The active carbon preferably has a specific surface area of at least 1,500 $m^2/g$, for example from 1,500 to 2,500 $m^2/g$ and particularly from 1,800 to 2,500 $m^2/g$. In particular, the active carbon preferably has a specific surface area of at least 2000 $m^2/g$.

Preferably, the active carbon has an improved adsorption performance by subjecting it to a steam activation treatment. Preferably, the active carbon is exposed to a steam at a temperature of at least 120° C., for example from 130 to 1000° C., particularly from 150 to 350° C. and at a pressure of at least 0.2 MPa, for example from 0.5 to 15 MPa and particularly from 1 to 15 MPa. The treatment time of the steam activation may be generally from 10 seconds to 50 hours, for example, from 10 minutes to 10 hours. During the activation, the active carbon may be heated in a furnace.

The surface of the active carbon may be impregnated with a cation. Examples of the cation include a metal ion, a metal oxide ion and an ammonium ion. Examples of the metal include a metal atom selected from Groups 1 to 13 of the Periodic Table of the Elements, for example, an alkaline metal (for example, Li, Na and K), an alkaline earth metal (for example, Mg and Ca), and Ti, Zr, V, Cr, Fe, Ni, Cu and Zn.

The high activation active carbon adjusted to acidic state (for example, hydrochloric acid acidity) is preferable. The acidic high activation active carbons can be produced by soaking, in an acid (particularly, hydrochloric acid), the active carbon which has been subjected to an activation treatment at a higher temperature than a general activation temperature and/or for a longer time than a general activation time. Alternatively the acidic high activation active carbons can be produced by flowing the acid through the active carbon.

The fluorocarboxylic acid having an ether bond may be a free form or a salt form.

Preferably the fluorocarboxylic acid having an ether bond is a carboxylic acid having an aliphatic group, particularly an aliphatic carboxylic acid having an aliphatic group (in particular, an alkyl group) which is partially or completely substituted with fluorine atoms. Particularly preferably, the fluorocarboxylic acid is a perfluorocarboxylic acid. Preferably the carbon atom of the fluorocarboxylic acid having an ether bond is from 5 to 30. Preferably, the fluorocarboxylic acid having an ether bond has a monooxyfluoroalkylene group (the number of oxyfluoroalkylene groups is 1.) or a polyoxyfluoroalkylene group (the number of oxyfluoroalkylene groups is two or more.) as an ether group. The number of oxyfluoroalkylene groups in the fluorocarboxylic acid may be from 1 to 10, particularly from 1 to 5. Preferably, the oxyfluoroalkylene group is a branched or linear chain and has 2-5 carbon atoms.

The fluorocarboxylic acid having an ether bond may be represented by the following general formula (I):

$$X\text{—Rf-COOH} \tag{I}$$

wherein X is a hydrogen atom, a fluorine atom or a chlorine atom, and

Rf is a group having a linear or branched monooxyfluoroalkylene group or polyoxyfluoroalkylene group having 4-20 carbon atoms.

Rf is preferably a group of the formula:

$$-A^1O\text{-}(A^2O)_{n\text{-}}A^3-$$

wherein $A^1O$ is an oxyfluoroalkylene group having 1-10 carbon atoms,
$A^2O$ is an oxyfluoroalkylene group having 2-5 carbon atoms,
$A^3$ is a fluoroalkylene group having 1-4 carbon atoms, and
n is an integer of 0 to 5, preferably an integer of 1 to 4.

Preferably, $A^1O$ is an oxyperfluoroalkylene group, $A^2O$ is an oxyperfluoroalkylene group, and $A^3$ is a perfluoroalkylene group. Preferably, the number of carbon atoms of Rf is from 4 to 14.

The fluorocarboxylic acid is preferably represented by the following general formula (II):

$$X\text{—}(CF_2)_m\text{—}O\text{—}(CF(CF_3)CF_2O)_n\text{—}CF(\text{—}Y)(CF_2)_p COOH \tag{II}$$

wherein X is a hydrogen atom, a fluorine atom or a chlorine atom,
Y is a hydrogen atom, a fluorine atom or $CF_3$,
m is an integer of 1 to 10,
n is an integer of 0 to 5, and
p is 0 or 1.

Preferably n is from 1 to 4.

The fluorocarboxylic acid may be represented by the following formula (IIa) or (IIb):

$$X\text{—}(CF_2)_m\text{—}O\text{—}(CF(CF_3)CF_2O)_n\text{—}CF(CF_3)COOH \tag{IIa}$$

wherein X is a hydrogen atom, a fluorine atom or a chlorine atom,
m is an integer of 1 to 10, and
n is an integer of 0 to 5, or $$X\text{—}(CF_2)_m\text{—}O\text{—}(CF(CF_3)CF_2O)_n\text{—}CHFCF_2COOH \tag{IIb}$$

wherein X is a hydrogen atom, a fluorine atom or a chlorine atom,
m is an integer of 1 to 10, and
n is an integer of 0 to 5.

Examples of the salt of the fluorocarboxylic acid include a metal salt, an ammonium salt and an amine salt. Examples of the metal salt include a salt of an alkaline metal, for example, lithium, sodium and potassium (Group 1 of the Periodic Table), or a salt of an alkaline earth metal, for example, calcium and magnesium (Group 2 of the Periodic Table).

Specific Examples of the fluorocarboxylic acid are as follows:

2,3,3,3-tetrafluoro-2-[1,1,2,3,3,3-hexafluoro-2-(trifluoromethoxy)propoxy]-propanoic acid [$CF_3$—O—(CF($CF_3$)$CF_2$O)—CF($CF_3$)COOH],
$CHF_2$—O—(CF($CF_3$)$CF_2$O)—CF($CF_3$)COOH,
$CF_3$—O—(CF($CF_3$)$CF_2$O)$_2$—CF($CF_3$)COOH,
$CF_3$—O—(CF($CF_3$)$CF_2$O)$_2$—CF($CF_3$)COOH,
$CF_3$—O—(CF($CF_3$)$CF_2$O)—CHFCF$_2$COOH, and
$CHF_2$—O—(CF($CF_3$)$CF_2$O)$_3$—CHFCF$_2$COOH.

Specific examples of the salts of the fluorocarboxylic acid include an alkali metal salt and ammonium salt of the specific examples of the fluorocarboxylic acid, particularly ammonium 2,3,3,3-tetrafluoro-2-[1,1,2,3,3,3-hexafluoro-2-(trifluoromethoxy)propoxy]-propanoate salt.

The fluorocarboxylic acid generally one having a function as a surface active agent.

In the present invention, adsorption and desorption of the fluorocarboxylic acid can be performed with using an active carbon. The fluorocarboxylic acid can be recovered by desorbing the adsorbed substances such as the fluorocarboxylic acid from the active carbon.

(1) Adsorption

The concentration of the fluorocarboxylic acid in the liquid containing the fluorocarboxylic acid is generally from 0.01 ppm to 200, particularly from 10 to 100 ppm (based on weight).

The liquid containing the fluorocarboxylic acid may be adjusted to have pH of from 1 to 5 by adding an acid, for example, an inorganic acid such as hydrochloric acid, before the adsorption.

The fluorocarboxylic acid is adsorbed in the active carbon by contacting the liquid containing the fluorocarboxylic acid with the active carbon. The temperature during the contact may be, for example, from 0 to 50° C. and the pressure may be, for example, from 0.1 to 10 atm, particularly 1 atm. The contact time may be from 0.1 seconds to 100 hours, for example, from 1 second to 1 hour, particularly from 30 seconds to 1 minute. The contact may be performed by either batch or flow process.

The adsorption rate of the fluorocarboxylic acid to the active carbon can be controlled by changing the pH of the liquid. The pH of the liquid may be from 1.5 to 13.5, for example, from 2 to 13.

The active carbon that has adsorbed can be separated from the liquid containing the fluorocarboxylic acid by, for example, a filtration.

(2) Desorption

Desorption of the fluorocarboxylic acid having an ether bond (from the active carbon) can be performed by heating the active carbon, which has adsorbed the fluorocarboxylic acid having an ether bond, to a temperature at which the fluorocarboxylic acid and water make an azeotropic distillation, for example, at least 99° C., particularly 99 to 145° C. The pressure may be from 0.1 to 10 atm, particularly 1 atm. The heating time may be generally from 1 second to 10 hours, for example, from 1 minute to 2 hours.

The use of temperature of at least 150° C. might give a recovery loss so that thermal decomposition tends to become significant.

When the azeotrope mixture is cooled (for example, to 25° C.), a layer of the fluorocarboxylic acid is separated from a layer of water.

EXAMPLES

Hereinafter, examples wherein a fluorocarboxylic acid having an ether bond in a liquid phase is adsorbed by an active carbon and examples wherein the active carbon, which has adsorbed the fluorocarboxylic acid having an ether bond, is heated by a dryer so that the adsorbed substances is desorbed from the active carbon.

In some of the following examples, each of six types of active carbons having different specific surface areas, which were prepared from the same material (coconut shell), was used.

| | Specific Surface Area | Product name |
|---|---|---|
| General Carbon 1 | 1150 | DIAHOPE M006 F-400, manufactured by Calgon Mitsubishi Chemical Corporation |
| General Carbon 2 | 1180 | Shirasagi WH, manufactured by Japan EnviroChemicals, Limited |

-continued

| | Specific Surface Area | Product name |
|---|---|---|
| Highly Activated Carbon 1 | 2300 | Kuraray Coal NK-261, manufactured by Kuraray Chemical Co., Ltd. |
| Highly Activated Carbon 2 | 2000 | D-2000, manufactured by Calgon Mitsubishi Chemical Corporation |
| Highly Activated Carbon 3 | 1800 | — |
| Highly Activated Carbon 4 | 1500 | — |

Example 1

Into a 500 cc glass bottle, each of active carbons (0.1 g) was charged and then 300 cc of aqueous solution containing 100 ppm of 2,3,3,3-tetrafluoro-2-[1,1,2,3,3,3-hexafluoro-2-(trifluoromethoxy)propoxy]-propanoic acid, which was adjusted to pH 2, was charged. The bottle was shaken at a temperature of 25° C. for 24 hours by a shaking apparatus, to adsorb 2,3,3,3-tetrafluoro-2-[1,1,2,3,3,3-hexafluoro-2-(trifluoromethoxy)propoxy]-propanoic acid by the active carbon. Then, an adsorption amount (an equilibrium amount of adsorption) was calculated from the concentrations of 2,3,3,3-tetrafluoro-2-[1,1,2,3,3,3-hexafluoro-2-(trifluoromethoxy)propoxy]-propanoic acid in the raw water and the treated aqueous solution. An adsorption rate of 2,3,3,3-tetrafluoro-2-[1,1,2,3,3,3-hexafluoro-2-(trifluoromethoxy)propoxy]-propanoic acid to each active carbon is shown in Table 1.

The adsorption rate (%) is given by:

[[(Concentration of 2,3,3,3-tetrafluoro-2-[1,1,2,3,3,3-hexafluoro-2-(trifluoromethoxy)propoxy]-propanoic acid in initial raw water [ppm])—(Concentration of 2,3,3,3-tetrafluoro-2-[1,1,2;3;3,3-hexafluoro-2-(trifluoromethoxy)-propoxy]-propanoic acid in treated water after adsorption [ppm])]×(Amount of raw water [g])]/[(Amount of used active carbon [g])×1,000,000]×100 [%].

TABLE 1

| Types of Active Carbon (coconut) | Specific Surface Area [m²/g] | Adsorption Rate [%] |
|---|---|---|
| Highly Activated Carbon 1 | 2300 | 25.4 |
| Highly Activated Carbon 2 | 2000 | 22.9 |
| Highly Activated Carbon 3 | 1800 | 19.5 |
| Highly Activated Carbon 4 | 1500 | 16.7 |
| General Carbon 1 | 1150 | 6.9 |
| General Carbon 2 | 1180 | 7.8 |

As shown in Table 1, the fact that there is a relationship between the adsorption rate and the specific surface area is admitted. It was also admitted that the adsorption rate of active carbons reaches at least 20%, when the active carbons have a specific surface area of at least 1,800 [m²/g].

Example 2

The same operation as in Example 1 was repeated except for using an ion-impregnated active carbon (Specific surface area: 500 m²/g). The adsorption rates of 2,3,3,3-Tetrafluoro-2-[1,1,2,3,3,3-hexafluoro-2-(trifluoromethoxy)propoxy]- propanoic acid in the active carbons classified based on the impregnated ions are shown in Table 2.

TABLE 2

| Impregnated Ion | Adsorption Rate [%] |
|---|---|
| MgO I | 12.3 |
| MgO II | 13.7 |
| Amines | 16.7 |

Example 3

An active carbon (Specific surface area: 500-2,000 m$^2$/g) (0.1 g), to which 2,3,3,3-tetrafluoro-2-[1,1,2,3,3,3-hexafluoro-2-(trifluoromethoxy)propoxy]-propanoic acid was adsorbed until reaching the breakthrough point, was charged into a dryer and left at a temperature of 99° C. for 48 hours. The desorption amount was taken as the same as an adsorption amount in adsorption again after the desorption.

The same procedure was repeated for perfluorohexanoic acid.

The results are shown in Tables 3 and 4.

TABLE 3

Adsorption and desorption amounts of 2,3,3,3-tetrafluoro-2-[1,1,2,3,3,3-hexafluoro-2-(trifluoromethoxy)propoxy]-propanoic acid by active carbon

| Active carbon type | Adsorption amount | Desorption amount | Desorption rate [%] |
|---|---|---|---|
| Highly Activated Carbon 1 | 0.0254 | 0.0151 | 59.4 |
| Highly Activated Carbon 2 | 0.0228 | 0.0144 | 63.2 |
| Highly Activated Carbon 3 | 0.0194 | 0.0094 | 48.5 |
| Highly Activated Carbon 4 | 0.0168 | 0.0077 | 45.8 |
| General Carbon 1 | 0.0068 | 0.0043 | 63.2 |
| General Carbon 2 | 0.0078 | 0.0049 | 62.8 |

TABLE 4

Adsorption and desorption amounts of perfluorohexanoic acid by active carbon

| Active carbon type | Adsorption amount | Desorption amount | Desorption rate [%] |
|---|---|---|---|
| Highly Activated Carbon 1 | 0.0227 | 0.0117 | 51.5 |
| Highly Activated Carbon 2 | 0.0219 | 0.0121 | 55.3 |
| Highly Activated Carbon 3 | 0.0211 | 0.0074 | 35.1 |
| Highly Activated Carbon 4 | 0.0180 | 0.0059 | 32.8 |
| General Carbon 1 | 0.0085 | 0.0038 | 44.7 |
| General Carbon 2 | 0.0081 | 0.0034 | 42.0 |

Tables 3 and 4 shows that 2,3,3,3-tetrafluoro-2-[1,1,2,3,3,3-hexafluoro-2-(trifluoromethoxy)propoxy]-propanoic acid having easy tendency of evaporation in azeotrope has a higher desorption.

Example 4

The same operation as in Example 1 was repeated by using an active carbon (Specific surface area: 700 m$^2$/g) and 2,3,3,3-tetrafluoro-2-[1,1,2,3,3,3-hexafluoro-2-(trifluoromethoxy)propoxy]-propanoic acid, and the relationship between the pH value and the adsorption rate was determined. Adjustment of pH was performed by adding an acid (hydrochloric acid, sulfuric acid or nitric acid) or a base (sodium hydroxide).

The results are shown in Table 5.

TABLE 5

| pH | Adsorption Rate [%] |
|---|---|
| 2.0 | 6.9 |
| 11.0 | 1.8 |

Example 5

A batch adsorption test of 2,3,3,3-tetrafluoro-2-[1,1,2,3,3,3-hexafluoro-2-(trifluoromethoxy)propoxy]-propanoic acid was conducted by using highly activated active carbon adjusted to acidic state by hydrochloric acid (Specific surface area: 2,000 m$^2$/g) and highly activated active carbon adjusted to neutral state (Specific surface area: 2,000 m$^2$/g).

The results are shown in Tables 6 and 7 and FIG. 1.

The highly activated active carbon adjusted to acidic state has an improved adsorption rate in comparison with the highly activated active carbon adjusted to neutral state.

TABLE 6

Adsorption performance of highly activated active carbon adjusted to neutral state

| Equilibrium concentration [ppm] | Adsorption rate [%] | Active carbon amount [g] | pH |
|---|---|---|---|
| 30.1 | 11.8 | 0.1 | 3.6 |
| 57.4 | 15.9 | 0.1 | 3.6 |
| 162.4 | 32.8 | 0.1 | 3.6 |

TABLE 7

Adsorption performance of highly activated active carbon adjusted to acidic state

| Equilibrium concentration [ppm] | Adsorption rate [%] | Active carbon amount [g] | pH |
|---|---|---|---|
| 30.4 | 19.6 | 0.1 | 3.6 |
| 70.1 | 28.9 | 0.1 | 3.6 |
| 179.5 | 43.2 | 0.1 | 3.6 |

Industrial Applicability

The present invention provides an adsorption process in which high adsorption of the fluorocarboxylic acid having an ether bond can be attained without any morphological change of the fluorocarboxylic acid having an ether bond by the use of active carbon, and a desorption process in which active carbon and adsorbed substances can be recycled by desorbing the adsorbed substances from the active carbon. Although it is not intended to limit the present invention, the fluorocarboxylic acid having an ether bond, which are contained in industrial waste water and have possibility to cause environmental problems in the future, can be highly recovered from a liquid phase and recycled according to the present invention.

The invention claimed is:
1. A method of adsorbing a fluorocarboxylic acid having an ether bond, which comprises contacting an aqueous containing fluorocarboxylic acid solution with an acidic high activa- tion active carbon to adsorb the fluorocarboxylic acid by the acidic high activation active carbon, wherein the acidic high activation active carbon is produced by soaking, in an acid, an active carbon, or by flowing the acid through the active carbon, in which the active carbon has been subjected to an activation treatment, and wherein the acidic high activation active carbon has an adsorption rate of the fluorocarboxylic acid of 10% or more; and wherein the fluorocarboxylic acid having an ether bond is represented by the following general formula (I):

X—Rf—COOH  (I)

wherein X is a hydrogen atom, a fluorine atom or a chlorine atom, and

Rf is a group having a linear or branched monooxyfluoroalkylene group or polyoxyfluoroalkylene group having 4-20 carbon atoms.

2. The method according to claim 1, wherein the acidic high activation active carbon has a specific surface area of at least 1500 m²/g.

3. The method according to claim 1, wherein the pH of the acid solution contacting with the active carbon during the preparation of the active carbon is adjusted to at most 4.

4. The method according to claim 1, wherein Rf is a group of the formula:

$-A^1O-(A^2O)_n-A^3-$ wherein $A^1O$ is an oxyfluoroalkylene group having 1-10 carbon atoms, $A^2O$ is an oxyfluoroalkylene group having 2-5 carbon atoms, $A^3$ is a fluoroalkylene group having 1-4 carbon atoms, and n is an integer of 0 to 5, preferably an integer of 1 to 4.

5. The method according to claim 1, wherein the fluorocarboxylic acid is represented by the following general formula (II):

X—(CF$_2$)$_m$—O—(CF(CF$_3$)CF$_2$O)$_n$—CF(—Y)(CF$_2$)$_p$COOH  (II)

wherein X is a hydrogen atom, a fluorine atom or a chlorine atom,

Y is a hydrogen atom, a fluorine atom or CF$_3$, m is an integer of 1 to 10, n is an integer of 0 to 5, and p is 0 or 1.

6. The method according to claim 1, wherein the fluorocarboxylic acid is represented by the following formula (IIa) or (IIb):

X—(CF$_2$)$_m$—O—(CF(CF$_3$)CF$_2$O)$_n$—CF(CF$_3$)COOH  (IIa)

wherein X is a hydrogen atom, a fluorine atom or a chlorine atom, m is an integer of 1 to 10, and n is an integer of 0 to 5, or X—(CF$_2$)$_m$—O—(CF(CF$_3$)CF$_2$O)$_n$—CHFCF$_2$COOH  (IIb)

wherein X is a hydrogen atom, a fluorine atom or a chlorine atom, m is an integer of 1 to 10, and n is an integer of 0 to 5.

7. The method according to claim 1, wherein the fluorocarboxylic acid having an ether is CF$_3$—O—CF(CF$_3$)CF$_2$O—CF(CF$_3$)COOH.

8. The method according to claim 1, wherein the fluorocarboxylic acid is 2,3,3,3-tetrafluoro-2-[1,1,2,3,3,3-hexafluoro-2-(trifluoromethoxy)propoxyl]-propanoic acid or salts thereof.

9. A method of recovering a fluorocarboxylic acid having an ether bond, which comprises desorbing the fluorocarboxylic acid having an ether bond from an acidic high activation active carbon, which has adsorbed the fluorocarboxylic acid b the use of azeotropy, with water to collect the fluorocarboxylic acid, wherein the acidic high activation active carbon has an adsorption rate of the fluorocarboxylic acid of 10% or more; and wherein the fluorocarboxylic acid having an ether bond is represented by the following general formula (I):

X—Rf—COOH  (I)

wherein X is a hydrogen atom, a fluorine atom or a chlorine atom, and

Rf is a group having a linear or branched monooxyfluoroalkylene group or polyoxyfluoroalkylene group having 4-20 carbon atoms.

10. The method according to claim 9, wherein Rf is a group of the formula:

$-A^1O-(A^2O)_n-A^3-$ wherein $A^1O$ is an oxyfluoroalkylene group having 1-10 carbon atoms, $A^2O$ is an oxyfluoroalkylene group having 2-5 carbon atoms, $A^3$ is a fluoroalkylene group having 1-4 carbon atoms, and n is an integer of 0 to 5, preferably an integer of 1 to 4.

11. The method according to claim 9, wherein the fluorocarboxylic acid is represented by the following general formula (II):

X—(CF$_2$)$_m$—O—(CF(CF$_3$)CF$_2$O)$_n$—CF(—Y)(CF$_2$)$_p$COOH  (II)

wherein X is a hydrogen atom, a fluorine atom or a chlorine atom,

Y is a hydrogen atom, a fluorine atom or CF$_3$, m is an integer of 1 to 10, n is an integer of 0 to 5, and p is 0 or 1.

12. The method according to claim 9, wherein the fluorocarboxylic acid is represented by the following formula (IIa) or (IIb):

X—(CF$_2$)$_m$—O—(CF(CF$_3$)CF$_2$O)$_n$—CF(CF$_3$)COOH  (IIa)

wherein X is a hydrogen atom, a fluorine atom or a chlorine atom, m is an integer of 1 to 10, and n is an integer of 0 to 5, or X—(CF$_2$)$_m$—O—(CF(CF$_3$)CF$_2$O)$_n$—CHFCF$_2$COOH  (IIb)

wherein X is a hydrogen atom, a fluorine atom or a chlorine atom, m is an integer of 1 to 10, and n is an integer of 0 to 5.

13. The method according to claim 9, wherein the fluorocarboxylic acid having an ether is CF$_3$—O—CF(CF$_3$)CF$_2$O—CF(CF$_3$)COOH.

14. The method according to claim 9, wherein the fluorocarboxylic acid is 2,3,3,3-tetrafluoro-2-[1,1,2,3,3,3-hexafluoro-2-(trifluoromethoxy)propoxy]-propanoic acid or salts thereof.

15. The method according to claim 1, wherein the activation treatment is a steam activation treatment.

16. The method according to claim 1, which further comprises adjusting a pH level of the liquid containing the fluorocarboxyclic acid by adding an acid.

* * * * *